United States Patent [19]

Pedersen

[11] Patent Number: 4,522,810

[45] Date of Patent: Jun. 11, 1985

[54] FELINE CALICIVIRUS VACCINE

[75] Inventor: Niels C. Pedersen, Winters, Calif.

[73] Assignee: The Regents of the University of California, Berkeley, Calif.

[21] Appl. No.: 448,098

[22] Filed: Dec. 9, 1982

[51] Int. Cl.$^3$ .......................... A61K 39/12; C12N 7/00
[52] U.S. Cl. ........................................ 424/89; 435/235
[58] Field of Search ........................................... 424/89

[56] References Cited

U.S. PATENT DOCUMENTS

| | | | |
|---|---|---|---|
| 3,937,812 | 2/1976 | Bittle et al. | 424/89 |
| 3,944,469 | 3/1976 | Bittle et al. | 424/89 |
| 4,264,587 | 4/1981 | Pederson et al. | 424/89 |

OTHER PUBLICATIONS

Burki et al., Infect. Immun., 14(4), 1976, 876–881.
Gaskell, C. J. et al., Res. Vet. Sci., (England), Jan. 1982, 32(1), pp. 23–26.

*Primary Examiner*—Sidney Marantz
*Assistant Examiner*—Shawn P. Foley
*Attorney, Agent, or Firm*—Bertram I. Rowland

[57] ABSTRACT

Feline calicivirus FCV-2280 is used in a live, attenuated or killed form as a vaccine, either by itself or in combination with another feline calicivirus strain. The virus may be administered in an effective dosage in a variety of ways.

The virus FCV-2280 has been deposited at the A.T.C.C. on Dec. 9, 1982, and given accession No. VR 2057.

10 Claims, No Drawings

FELINE CALICIVIRUS VACCINE

BACKGROUND OF THE INVENTION

1. Field of the Invention

Caliciviruses are reported as an important cause of illness in cats. A wide variety of symptoms are observed such as fever, rhinitis, sneezing, mild conjunctivitis, occular discharge, vesicles in the external nares, oral mucosa or on the tongue, pneumonia, tracheal bronchitis, diarrhea, muscle soreness, stiff gate, and hyperesthesia. It should be noted that such signs, although reportedly common in natural cases, are not always prominent in experimental infections. It would appear that various field strains of feline calicivirus (FCV) either differ in their disease causing potential or that concurrent infection with other agents influences the disease symptoms.

Feline calicivirus strains have been identified as either neutralized by most antiserum or elicit antibodies that neutralize most other strains. One such strain, FCV-F9 is neutralized by antisera to many of the fourteen field isolates that were tested and FCV-F9 antiserum in turn neutralized all fourteen strains. For this reason, FCV-F9 was proposed as a reference strain. While the vaccines from FCV-F9 and other commercially available vaccines provide protection from most field isolates, it is not true that these vaccines prevent infection from all strains. There is, therefore, continued interest in developing a vaccine, which by itself or in combination with other vaccines would provide the desired protection upon vaccination of a cat.

2. Description of the Prior Art

U.S. Pat. No. 4,264,587 describes a vaccine for feline leukemia viremia. Kalunda et al. AJVR (1975) 36:353–356 describes the properties of the strain FCV-F9 as a vaccine. See also Bittle, et al., Ibid. (1976) 37:275–278. The strain FCV-M8 and its use as a vaccine is described by Davis and Beckenhauer, VM/SAC (1976) 71:1405–1410. The strain FCV-255 is described by Povey et al., JAVMA (1980) 177:347–350 (This particular strain is not designated in the reference.)

SUMMARY OF THE INVENTION

A feline calicivirus is provided from the strain FCV-2280 which is shown to provide broad spectrum protection against FCV infection and may be used by itself or in combination with other strains as a vaccine. Conventional administration may be employed.

DESCRIPTION OF THE SPECIFIC EMBODIMENTS

Vaccines are provided based on the use of FCV strain FCV-2280. The virus can be grown in conventional ways, particularly on feline cell monolayers, such as Crandall, fetal kidney cells, FC-0009 (available from Naval Biologics) or the like. For growth of the virus, the cell monolayers are infected at a high multiplicity of infection and the cells maintained until lysis occurs. After lysis of the cells, the supernant may be freed of cellular debris, fetal calf serum removed and the residual fluid concentrated to the desired concentration. The concentation will usually have a tissue culture infectious dose of $TCID_{50}$ of at least about $10^5$, usually at least about $10^6$.

As a vaccine, the FCV-2280 may be used by itself or in combination with other feline calicivirus strains finding use as vaccines, such as FCV-255, -682024, -F9, -M8, etc. The FCV-2280 may be administered oronasally, subcutaneously or intramuscularly. Killed vaccine will only be administered in the latter two ways, while the three ways will be applied for live or modified live vaccine. Adjuvant will not be employed with live vaccine, but will find use particularly with subcutaneous and intramuscular injections with killed vaccine to enhance immune response. Various adjuvants include aluminum hydroxide adjuvant (U.S. Pat. No. 49,036) oil based adjuvants e.g. mannide monooleate and paraffin in volume proportion of 1.5:8.5, copolymers, etc. While the proportions of the adjuvant to the virus containing medium may be varied widely, conveniently equal portions may be employed. The amount of virus as protein per dose will generally be in the range of about 1 to 2 $\mu g$ of protein.

For attenuation of the virus one normally looks for strains which have become naturally attenuated or in some instances may be attenuated by passage at elevated temperatures or by contact with mutagens. Various mutagenic agents are known, such as ultraviolet light, ethyl methanesulfonate, as well as many of the agents for inactivating viruses. The difference between inactivation and attenuation can be frequently one of degree. Inactivation agents include formalin, phenol, beta-lactopropionate, ultra-violet light, heat, psoralens, platinum complexes, or other viricidal agents, etc. The methods for inactivating viruses have been amply described in the literature. See, for example U.S. Pat. No. 2,064,587 beginning with column 3, lines 61ff.

The calicivirus strain FCV-2280 was isolated from the blood of a kitten demonstating high fever and shifting limb lameness. In a kitten colony of Dr. N. C. Pedersen, School of Veterinary Medicine, University of California, Davis, Calif., the virus was initially propagated in Felis catus whole fetus cells (fcwf-4) and the virus passaged three more times in tissue culture and then stored at $-70°$ C. The virus produces a stereotyped illness characterized by fever, viremia and lameness.

Besides use as a vaccine, the virus can be used in assays for detecting the presence of antibodies to the virus, as an antigen for producing serum which may be used in diagnostic arrays, and in the preparation of labelled reagents for use in assays.

The following examples are offered by way of illustration and not by way of limitation.

EXPERIMENTAL

Viruses-FCF-2280 was isolated from the blood of a kitten demonstrating high fever, and shifting limb lameness. The kitten was obtained from the School of Veterinary Medicine, University of California, Davis, (Pederson), feline leukemia virus free breeding colony. The disease in this kitten was typical of an illness seen to occur routinely in many 8 to 12 week-old kittens from this colony over a period of 2 years. Following initial propagation in Felis catus whole fetus cells (fcwf-4), the virus was passaged 3 more times in tissue culture and then stored at $-70°$ C. for use in these studies. FCV-LLK was isolated from the blood of an 8 week-old Abyssinian kitten in the cattery of the Department of Clinical Studies, Ontario Veterinary College, Guelph, Ontario, Canada (Laliberte). Initial isolation of this strain was made on Crandall feline fetal fibroblast cells. It was then passaged 3 times on fcwf-4 cells, and then stored at $-70°$ C. for use in these studies. FCV-F9, in a modified virulence form, was isolated from a popular intramuscularly administered feline panleukopeniacalicivirus-rhinotracheitis virus vaccine. Similarly, FCV-M8 was isolated from a commonly used intranasally administered feline rhinotracheitis-calicivirus vaccine. Following reconstitution of the vaccines, the ampules were heated to 56° C. for 30 minutes to inactivate the live feline rhinotracheitis virus component, then a small aliquot of the material was exposed to fcwf-4 cells. Vaccine strains were passaged 3 times in fcwf-4 cells, then stored at −70° C. FCV-255, a virulent field strain used in an inactivated form in one vaccine, was available from Dr. Fred Scott, Cornell University, Ithaca, N.Y.

Serology-Virus neutralizing (VN) antibodies to FCV were measured in the following manner: 10 to 100 $TCID_{100}$ of FCV in 0.1 ml tissue culture media was mixed with serial two-fold dilutions (in 0.1 ml) in tissue culture media of the test serum. The mixture was allowed to interact for 30 min. at 37° C., then overlayed on fcwf-4 fetal cat cells grown in 96 well disposable microtiter culture plates. Cytopathic effect was observed with phase contrast microscopy at 48 to 72 hours post-infection. The antibody titer was expressed as the reciprocal of the highest dilution that prevented cytopathic effect.

Experimental Animals-Specific pathogen free (SPF) kittens, 8 to 24 weeks of age, were obtained from Liberty Laboratories, Liberty Corners, N.J., and from the colony of Drs. Q. Rogers and J. Morris, University of California, Davis, Calif. Conventionally reared kittens were obtained from the feline leukemia virus free colony, Feline Leukemia Research Laboratory, University of California, Davis. Experimental animals were housed in isolation units provided by the Animal Resources Services, University of California, Davis.

Experimental Infection-in order to characterize the disease caused by FCV-2280 specific pathogen free SPF kittens were infected oronasally with a $1 \times 10^6$ $TCID_{50}$ of tissue culture propagated virus. Four kittens were infected. Rectal temperatures were taken daily and complete blood counts were done every second day. In addition, the kittens were closely observed for outward signs of illness.

Kittens infected with either isolate developed a fever between 48–72 hrs. post exposure. The fever persisted for 48–72 hrs. during which time critical signs were also observed. Simultaneous with the onset of fever, all the kittens became depressed and anorexic to varying degrees usually in proportion to the magnitude of the febrile response. Within hours of the onset of depression the kittens demonstrated generalized sickness or more localized muscular skeletal abnormalities. All clinical signs disappeared after 48–72 hours and no residual effects were noted.

Physical examination during the period of critical illness demonstrated a generalized hyperesthesia upon palpation, pain upon manipulation of joints and in some cases a mild redness to the skin over the tarsal joints. No other physical abnormalities were observed. Leukopenia was detected in some of the kittens. The leukopenia was mainly due to a decrease in the absolute polymorphonuclear neutrophil counts, although lymphocytes were also depressed to some extent.

Virus was readily isolated from the blood of kittens during the brief 48–72 period when the rectal temperatures were elevated.

Histopathologic-infected kittens were sacrificed, tissues taken from a large number of organs, fixed in formalin solution or quick frozen for a cryostat microtone sectioning and fluorescent antibody staining. Fluorescent antibody staining with a cat anti-FCV-2280 IgG conjugate was done on representative cryostat-microtone prepared acetone fixed tissue sections. Virus was identified only within the spleen and to a lesser extent in the mesenteric lymph nodes.

Serologic Study-Serum virus neutralizing (VN) antibody titers to FCV-2280, FCV-LLK, FCV-F9, and FCV-M8 were measured at intervals after infection in five kittens challenged with FCV-2280. Cats infected with FCV-2280 developed VN antibodies to FCV-LLK, FCV-F9 and FCV-M8. Eleven days after the initial challenge, kittens infected with FCV-2280 were infected with FCV-LLK. The cats originally infected with FCV-2280 were resistant to disease from challenge with FCV-LLK.

In the next study, four sixteen week old SPF kittens were vaccinated intramuscularly with a commercial FCV vaccine containing modified live FCV-F9. The virus neutralizing antibody titers against FCV-9, FCV-2280 and FCV-LLK were determined at 28 days post vaccination.

TABLE 1

Virus Neutralizing Antibody Titers in the Serum of Kittens Immunized with a Single Dose of Modified Live FCV-F9 Vaccine and Challenged with Either FCV-2280 or FCV-LLK on day 28.

| Cat # | Days post-vaccination | FCV Challenge strain | VN Antibody Titers in Serum to FCV-2280, FCV-LLK, and FCV-F9 | | |
|---|---|---|---|---|---|
| | | | FCV-2280 | FCV-LLK | FCV-F9 |
| 2412 | 0 | FCV-2280 | neg | neg | neg |
| | 28 | | neg | 10 | 320 |
| | 42 | | 80 | 320 | 20,480 |
| 2416 | 0 | FCV-2280 | neg | neg | neg |
| | 28 | | neg | 10 | 320 |
| | 42 | | 10,240 | 640 | 20,480 |
| 2417 | 0 | FCV-LLK | neg | neg | neg |
| | 28 | | neg | 0 | 640 |
| | 42 | | neg | 5120 | 20,480 |
| 2425 | 0 | FCV-LLK | neg | neg | neg |
| | 28 | | neg | 10 | 640 |
| | 42 | | 10 | 640 | 20,480 |

None of the four vaccinated kittens developed VN antibodies against FCV-2280. There were good VN titers, however, to FCV-F9, indicating that the vaccination had been adequate. Twenty-eight days post vaccination two kittens were challenged oronasally with FCV-2280. Kittens infected with FCV-2280 developed a typical course of illness. There was an amnestic immune response following challenge.

FCV-2280 was isolated from a cattery that had been routinely vaccinated with modified live FCV-F9. Five 12 to 16-week old kittens from this cattery were therefore tested for VN antibodies to FCV-2280, FCV-LLK, FCV-F9, FCV-M8, and FCV-255. These kittens had been vaccinated with the commercial FCV-F9 containing vaccine at 8, 11 and 14 weeks of age. All five of these kittens had VN antibodies to FCV-LLK, FDV-F9, FCV-255, and FCV-M8 in their post vaccination serum. Only 2/5 kittens, however, had titers to FCV-2280 and these were at relatively low levels (1:10, 1:40).

Although FCV-F9 vaccine strain given IM did not produce much immunity to FCV-2280, it was possible that it would do so if given by a more natural route, such as oronasal. Live FCV-F9 was therefore given oronasally to 4 adolescent SPF cats. All of these cats developed VN antibodies in the same pattern as the intramuscularly vaccinated cats.

The ability of oronasal vaccines containing FCV-M8 to cross-protect against FCV-2280 and FCV-LLK was investigated. Four SPF adolescent cats were oronasally immunized with a single commercial dose of FCV-M8 containing vaccine, and virus neutralizing titers against FCV-2280, FCV-LLK, and FCV-M8 were measured 3 weeks later.

TABLE 2

Virus Neutralizing Antibody Titers in Serum from Kittens Immunized Oronasally with a Single Dose of FCV-M8 Containing Vaccine.

| Cat # | Days post-vaccination | VN Antibody Titers in Serum to FCV-M8, FCV-LLK, and FCV-2280 | | |
|---|---|---|---|---|
| | | FCV-M8 | FCV-LLK | FCV-2280 |
| 233 | 0 | neg | neg | neg |
| | 18 | 1280 | neg | neg |
| 234 | 0 | neg | neg | neg |
| | 18 | 1280 | neg | neg |
| 234A | 0 | neg | neg | neg |
| | 18 | 160 | neg | neg |
| 236 | 0 | neg | neg | neg |
| | 18 | 640 | neg | neg |

FCV-M8 vaccination produced high VN titers to FCV-M8, but no antibodies to FCV-2280 or FCV-LLK. Kittens vaccinated with FCV-M8 vaccine were still susceptible to FCV-2280 and FCV-LLK, infection when challenged 18 days later.

The final study dealt with FCV-255, a highly pneumotrophic field strain used in a killed FCV vaccine. Five 10 to 12 week-old SPF kittens were vaccinated 2 times at 3 week intervals with a commercial inactivated FCV-255 containing vaccine. Five littermate kittens were also vaccinated oronasally with a single dose ($1\times10^6$ $TCID_{50}$) of live FCV-255. Virus neutralizing antibody titers to FCV-2280, FCV-LLK, FCV-255, FCV-F9, and FCV-M8 were then measured in serum collected 35 days after initial vaccination.

TABLE 3

Post-Vaccination Virus Neutralizing Antibody Titers of Specific Pathogen Free Kittens Vaccinated with Virulent Live and FCV-255 and an Inactivated Commercial FCV-255 Vaccine.

| Cat # | Vaccine | Post Vaccination Virus Neutralizing Antibody Titers | | | | |
|---|---|---|---|---|---|---|
| | | FCV-F9 | FCV-2280 | FCV-LLK | FCV-255 | FCV-M8 |
| CL5 | Live FCV-255 | 160 | neg | 320 | ≧1280 | 20 |
| CT3 | " | 320 | neg | ≧1280 | ≧1280 | 80 |
| CV3 | " | 160 | neg | 160 | 320 | 10 |
| CV3 | " | 320 | neg | 80 | ≧1280 | 40 |
| DC1 | " | 40 | neg | 640 | 10,240 | 320 |
| CO3 | Killed FCV-255 | 80 | neg | 640 | 320 | 80 |
| CP4 | " | 80 | neg | ≧1280 | 320 | 10 |
| CW1 | " | 160 | neg | 2560 | 640 | 80 |
| CW4 | " | neg | neg | 40 | 80 | neg |
| DC2 | " | 20 | 10 | ≧1280 | 5120 | 20 |

Virus neutralizing antibody titers were comparable in FCV-255 killed and live-virus vaccinated groups, albeit live virus vaccinated cats had greater overall titers to all of the strains except FCV-2280. All kittens had VN antibodies to FCV-255, FCV-F9, FCV-M8, and FCV-LLK. Only 1/10 kittens, however, had VN antibodies to FCV-2280, and then only at low titer (1:10).

The above results demonstrate that the commercial vaccines which generally utilize one of three strains of FCV, namely FCV-F9, -M8 or -255 do not cross-protect against FCV-2280. Regardless of the method of application of the commercially available viruses and even where FCV-255 was given line oronasally, no protection against FCV-2280 was observed. Therefore, by having FCV-2280 as a vaccine, used by itself or in conjunction or other FCV employed vaccines, broader protection against viremia by feline caliciviruses is achieved.

Although the foregoing invention has been described in some detail by way of illustration and example for purposes of clarity of understanding, it will be obvious that certain changes and modifications may be practiced within the scope of the appended claims.

What is claimed is:

1. A vaccine for protection against viremia caused by feline calicivirus, said vaccine comprising the strain FCV-2280, in an effective amount to produce an immune response, and a physiologically acceptable carrier.

2. A vaccine according to claim 1 containing an adjuvant.

3. A vaccine according to any of claims 1 or 2, wherein said virus FCV-2280 is live.

4. A vaccine according to any of claims 1 or 2, wherein said virus FCV-2280 is attenuated.

5. A vaccine according to any of claims 1 or 2, wherein said virus FCV-2280 is inactivated.

6. A method for protecting a cat from feline calicivirus infection which comprises:

administering to said cat an effective dose of a vaccine according to any of claims 1 or 2.

7. A method according to claim 6, wherein said administering is oronasally.

8. A method according to claiim 6, wherein said administering is subcutaneously.

9. A method according to claim 6, wherein said administering is intramuscular.

10. A vaccine according to any of claims 1 or 2 including at least one feline calicivirus strain selected from the group consisting of FCV-F9, FCV-LLK, FCV-M8, and FCV-255, in addition to FCV-2280.

* * * * *